United States Patent
Deigner

(10) Patent No.: US 6,790,992 B2
(45) Date of Patent: Sep. 14, 2004

(54) SCYPHOSTATIN ANALOGUES AS SMASE INHIBITORS

(75) Inventor: Hans-Peter Deigner, Lampertsheim (DE)

(73) Assignee: Biofrontera Pharmaceuticals GmbH, Leverkusen (DE)

( * ) Notice: Subject to any disclaimer, the term of this patent is extended or adjusted under 35 U.S.C. 154(b) by 0 days.

(21) Appl. No.: 10/225,741

(22) Filed: Aug. 22, 2002

(65) Prior Publication Data

US 2004/0039046 A1 Feb. 26, 2004

(51) Int. Cl.⁷ .................. C07C 233/18; C07D 263/06; A01N 37/18; A01N 43/76; A61K 31/16
(52) U.S. Cl. ....................................... 564/217; 548/215
(58) Field of Search ........................... 564/217; 548/215

(56) References Cited

PUBLICATIONS

Database CAPLUS, Acc. No. 1997:528764, Tanaka et al., Journal of the American Chemical Society (1997), 119(33), p. 7871–7872 (abstract).*

* cited by examiner

*Primary Examiner*—Brian Davis
(74) *Attorney, Agent, or Firm*—Marianne Fuierer; Steven J. Hultquist; Yongzhi Yang

(57) ABSTRACT

The present invention relates to novel scyphostatin analogues, which distinguish themselves by acting as SMase inhibitors so that they are of therapeutic use for a number of diseases such as a HIV infection, neurodegenerative diseases, inflammatory diseases, apoplexy, ischemia, myocardial infarction or in the case of atherosclerosis.

15 Claims, 5 Drawing Sheets

SCYPHOSTATIN ANALOGUES AS SMASE INHIBITORS

The, present invention relates to novel scyphostatin analogues which stand out for acting as inhibitors of SMase so that they are therapeutically useful in connection with a number of diseases, such as an HIV infection, neurodegenerative diseases, inflammatory diseases, ischemia, myocardial infarction, apoplexy, or in the case of atherosclerosis.

Sphingomyelin (N-acyl-spingosyl-phosphoryl-choline, SM) is an integral constituent of both biological membranes and plasma lipoproteins and an important source of forming messenger substances ("second messenger") such as ceramide which is released following stimulation by enzymes ("sphingoxnyetin pathway"), This signal transmission by membrane sphingolipids has been studied intensively in the last few years. SM is metabolized by isoforms of an enzyme similar to phospholipase C, which is referred as sphingomyelinase (SMase). To date, five isotypes of SMase are known. Most mammalian cells are capable of transmitting signals through the SM pathway, the signal transmission being activated by both receptors such as tumor necrosis factor (TNF) receptors or interleukin-1 receptors, and stress, such as U.V. light, oxidants or radiation. The formation of ceramide is nowadays considered co-decisive for the introduction of vital cell processes, such as cell proliferation and apoptosis. This correlation between ceramide formation and apoptosis induction comprises an activation of respectively particular SMase isoforms which display their optimum pH in an acidic (acidic SMases; acid SMases, aSMases) and/or in a neutral environment (neutral SMases; nSMases).

Apoptosis, programmed cell death, proceeds in an irreversible sequence of morphological and biochemical changes. It is the most important regulative mechanism for eliminating no longer required cells during embryonic development and growth or irreparably damaged cells. Various noxious substances, such as TNF/NGF, heat shock, cytostatic agents, ionizing radiation, infections caused by viruses or bacteria, deprivation of various growth factors and cell membrane-permeable ceramides induce apoptosis in different cell types Ceramide as a "second messenger" is involved in programmed cell death in widely differing tissues. For example, it is involved in regulating signal transduction, which eventually results in apoptosis.

The ceramide-induced cell death might play a role in widely differing diseases, such as sepsis, atherosclerosis, neurodegenerative diseases, such as Alzheimer's disease, Parkinsons' disease, and infections caused by retroviruses, such as the HIV virus, ceramide-mediated apoptosis having to be assumed in each case.

An infection with the HIV virus, type 1 (HIV-1) together with changes in the cellular metabolism results in a loss of subpopulations of T-lymphocytes, in particular the CD4$^+$ helper cells. There is more and more evidence for the fact that the intracellular redox system, i.e. the equilibnrium between oxidants and antioxidants, HIV infection and lymphocyte-associated ceramide are correlated via the activation of the SM pathway. The ceramide signal system is also involved in the HIV infection when either the HIV expression is regulated or apoptosis is induced. It was possible to show that ceramide initiates the signal cascade resulting in the apoptosis of lymphocytes in HIV-infected patients. This is considered one of the main causes of T-lymphocyte reduction, which ultimately leads to the fully manifested clinical picture. This takes place by induction of apoptosis' by means of the CD95/APO-1/Fas-receptor/ligand system which activates aSMase and results in the ceramide production. If this is inhibited by treatment with L-carnitine, ceramide synthesis is prevented both in vitro and in vivo. In the final analysis, it seems that the state of the redox systems and the progress of ceramic metabolism permit predictions as to the, intensity of the infection.

Apoptosis also plays a major role in neuronal cell death. It is assumed that there is a direct connection between oxidative stress and the occurrence of neurodegenerative diseases. Cell death in neurodegenerative diseases which can be caused by oxidative stress can be traced back to intracellular signals for SMase activation and the resulting ceramide production, Oxidative stress is attributed a major role in triggering Parkinson's disease and Alzheimer's disease, for example. Although the mechanisms inducing these diseases are not yet fully clear, the affected brain centers of the diseased persons have an increased apoptosis rate which is presumably due to an increased ceramide concentration.

SM/ceramide is also involved in chronic or acute inflammatory diseases. Both sepsis and the consequences of septic shock as-well as multiorgan failure have developed into the main cause of death in critical care units. Based on clinical, experimental and epidermologic data, sepsis is nowadays considered an inflammatory response to infections showing signs of severe defective organic functions herein, TNFα is the central mediator for the development of septic shock. Septic patients have increased serum TNFα concentrations and also cell-associated ceramide concentrations. It was possible to show that there is a direct connection between ceramide and TNFα concentrations. Since TNFα causes intracellular ceramide formation, the inflammatory response falsely modulated by TNFα might be blocked in spite of increased TNFα concentrations in the plasma by adding, SMase inhibitors, which would reduce the ceramide formation. Observations, of similar quality were also made in the case of other cellular reactions triggering sepsis. It would be possible to control the apopotosis rate and thus treat septic patients by interfering with the sphingolipid metaoblism to thus control and/or reduce the ceramide production.

Finally, SM metabolites and SMase also play are role in atherogenesis. The (phospho)lipid-protein complex "low density lipoprotein" (LDL) is important for phospolipids and neutral lipids in the plasma and very susceptible to oxidative and enzymatic modification. The oxidative or enzymatic modification of LDL comprises a number of chemical and biophysical changes of the lipoprotein. The resulting modified LDL (mLDL) is considered the biologically relevant proatherogenic lipoprotein which contains an abundance of active components. Cellular defective regulations or the injury of endothelial cells by activation of the cellular suicide mechanism resulting in apoptosis are regarded as the key steps for the development of atherosclerotic plaques. It was found that mLDL plays a double role in the case of artherosclerosis: low doses of mLDL are involved in the proliferation and synthesis of the extracellular matrix of the smooth muscle cells (SMC) during the early stage of atherosclerosis. In the advanced stage, when there is sufficient mLDL in the plaque, it may induce apoptosis in the SMC.

This results in instability and ruptures of the plaques and thus in the clinical consequences of artherosclerosis. mLDL induces the proliferation and apoptosis of SMC, Although many mechanisms are unclear, ceramide appears to act as an effector of a cellular response caused by mmLDL. mmLDL is an oxidation product of LDL (mmLDL, minimally modified LDL). Following internalization and lysosomal degradation, mmLDL containing as such a considerable SM proportion, supplies a substrate for the ceramide formation and stimulates the SM/ceramide pathway. The reduction of the aSMase activity offers a possibility of modulating the mLDL-rnediated cell death.

The modulation of endogenous ceramide generation) above all the reduction thereof, is thus a central aspect for the development of new (preventive) therapeutic approaches. This can be effected by inhibiting the membrane-bound neutral sphingomylinase (N-Smase), for example. A natural inhibitor of sphingomylinase is known. It is scyphostatin (FIG. 1) which could be isolated from *Trichopeziza mollissima* in 1997 for the first time[1,2]. However, this inhibitor can hardly be used in medicine thus far since it is chemically and metabolically very unstable. Furthermore, there was no possibility of synthetically obtaining this inhibitor or analogues thereof.

Thus, the invention is substantially based on the technical problem of providing novel scyphostatin analogues which do not show the drawbacks of the naturally occurring scyphostatin, i.e. can be produced synthetically and display increased chemical and metabolic stability.

This technical problem is solved by providing the embodiments characterized in the claims.

For the first time, the present invention comprises the chemical synthesis of biologically active analogues of scyphostatin. The active substance can be optimized by varying the described stages. For example, the substitution of the fatty acid amide side chains is possible compared with the fermentation method. The authentic natural substance has a polyene as a substituent (trienoyl fragment) at a corresponding position. Said derivatives are sensitive to oxidation according to the present state of knowledge. The natural substance is also unstable in acid, which is not the case for the compounds according to the invention (intermediate stages and end compounds).

It was found surprisingly that when the below described scyphostatin analogues according to the invention are used, the drawbacks of the naturally occurring scyphostatin are avoided, i.e. due to a structure simpler than that of the natural compound they have above all an increased chemical and metabolic stability. Therefore, they are predominantly suited for treating diseases having an inflammatory component such as sepsis, diseases of the rheumatic form, atherosclerosis as well as neurodegenerative diseases and potentially apoptosis-mediated diseases such as Alzheimer's disease, Parkinson's disease, ischemia, apoplexy, myocardial infarction and AIDS.

Thus, the present invention relates to a compound of formula

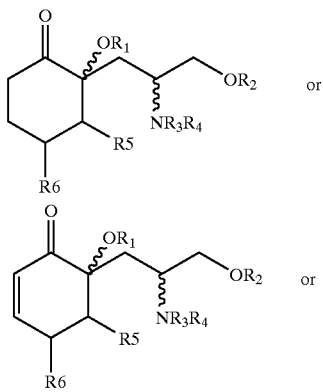

-continued

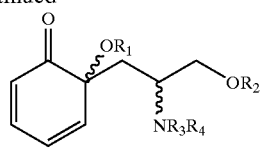

in which

R1, R2, R3, R5 and R6, which may be equal or different, represent a hydrogen atom, an OH group, an SH group, an O-alkyl, O-aryl, O-acyl, sulfonic acid, thioalkyl, thiophenyl, alkyl, alkenyl, alkinyl, aryl or acyl residue or a halogen; atom, and R4 is a fatty acid residue, a $C_6$–$C_{20}$ alkyl, alkenyl, alkinyl or aryl group, this compound being also characterized in that it can inhibit sphingomylinase (Smase) or a pharmaceutically compatible salt thereof.

In the present invention, the term "alkyl residue" for residues R1, R2, R3, R5 and R6 is an unbranched or branched $C_1$–$C_{12}$ alkyl chain, comprising the methyl, ethyl, n-propyl, isopropyl, n-butyl, isobutyl, sec.-butyl, tert.-butyl, n-pentyl, isopentyl, neopentyl, tert.-pentyl, 2-methylbutyl, n-hexyl, isohexyl, 2-methylpentyl, 2,3-dimethylbutyl, n-heptyl, 2-methylhexyl, 2,2-dimethylpentyl, 3,3-dirnethylpentyl, 3-ethylpentyl, n-octyl, 2,2-dimethylhexyl, 3,3-dimethylhexyl and 3-methyl-3-ethylpentyl group, for exaiple. Short alkyl chains, such as methyl, ethyl or propyl are preferred. However, cycloalkyl residues having 3 to 12 carbon atoms are also suited. Examples thereof are the cyclopropyl, cyclobutyl, cyclopentyl, cyclohexyl, cycloheptyl, cyclooctyl, cyclononyl, or cyclodecyl groups. Cyclopropyl, cyclobutyl, cyclopentyl and cyclohexyl are preferred. The same applies correspondingly to the "O-alkyl" or "thioalkyl" group.

As to the residue R4 the alkyl group has six to twenty C atoms. Here, groups are preferred which have more than 8 C atoms, such as the n-octyl group, n-nonyl group, n-decyl group, 3-methyl-3-ethylhexyl group, n-undecyl group, n-dodecyl group and cyclic alkyl residues, such as cyclooctyl, cyclononyl or cyclodecyl groups.

In the present invention, the term "alkenyl residue" for residues R1, R2, R3, R5 and R6 stands for unbranched or branched $C_{2-20}$ alkenyl residues. Examples thereof are vinyl, propenyl, isopropenyl, allyl, 2-methylallyl, butenyl or isobutenyl, hexenyl or isohexenyl, heptenyl or isoheptenyl, octenyl or isooctenyl groups. Vinyl, propenyl and isopropenyl are preferred. Cycloalkenyl residues having 4 to 30 carbon atoms are also suited, Examples thereof are cyclobutenyl, cyclopentenyl or cyclohexenyl, cycloheptenyl, cyclooctenyl, cyclononenyl or cyclodecenyl groups. Cyclobutenyl, cyclopentenyl or cyclohexenyl are preferred.

As to residue R4 the alkenyl group contains six to twenty C atoms. Alkenyl groups are preferred which have more than 8 C atoms, which may be linear, branched or cyclic. The same applies analogously to the alkinyl group. Polycyclic alkyl or alkenyl residues comprise norbornane, adamantane or berizvalene.

R1, R2, R3, R4, R5 and R6 can also be selected from any monocyclic or polycyclic $C_{6-20}$ aryl residues. Examples thereof are a carbocyclic, monocyclic residue, e.g. the phenyl group, a heterocyclic, monocyclic residue, e.g. the groups thienyl, furyl, pyranyl, pyrrolyl, imidazolyl, pyrazolyl, pyridyl, pyrazinyl, pyrimidinyl, pyrazinyl, thiazolyl, oxazolyl, furazannyl, pyrrolinyl, imidazolinyl, pyrazolinyl, thiazolinyl, triazolyl, tetazolyl as well as the positional isomer of the hetero atom or atoms which may comprise these groups, a residue consisting of carbocyclic condensed rings, e.g. the naphthyl group or phenanthrenyl groups, a residue consisting of condensed heterocyclic rings, e.g. benzofuranyl, benzothienyl, benzimidazolyl, benzothiazolyl. The aryl residues may be unsubstituted or substituted. Suitable substituents are e.g.:

$C_1$–$C_4$ alkyl, such as methyl, ethyl, propyl, etc.

substituted alkyl residues, such as trifluoromethyl, trifluorobutyl, pentafluoropropyl, pentafluorobutyl, pentafluoropentyl, heptafluorobutyl, or nonafluorobutyl group or 2-chloroethyl, acyloxy, such as acetoxy or a residue of formula:

—O—CO—$(CH_2)_n CH_2 H$, wherein n=1 to 5, alkoxy, such as methoxy, ethoxy, propytoxy, isopropyloxy, butyloxy, alkylthio, such as methylthio, ethylthio, propylthio, isopropylthio, butylthio, carbamoyl, alkenyl, such as vinyl, propenyl, alkinyl, such as ethinyl, propinyl, and hydroxy carboxy halogen, such as fluorine, chlorine, bromine, iodine $CONH_2$, CONH-alkyl CON(alkyl)$_2$ nitro amino $C_1$–$C_4$ alkylamino.

In the present invention, the term "acyl residue" stands for acetyl, propionyl, butyryl or benzoyl, for example. Correspondingly, the acyl residue can also be available as an O-acyl residue.

In the present invention, the term "fatty acid residue" stands for an aliphatic, saturated carboxylic acid having an almost exclusively unbranched carbon chain. The fatty acid residue preferably contains 6–30 C atoms, the fatty acid residue is preferably $CO(CH_2)_{14}CH_3$.

The term "halogen atom" stands for fluorine, chlorine, bromine or iodine atom, chlorine and bromine being preferred.

In a preferred embodiment of the compound according to the invention, the sulfonic acid residue is $OSO_2CH_3$.

In another preferred embodiment of the compound according to the invention, R1, R2, R3, R5 and R6 are a hydrogen atom each.

A compound according to the invention in which R4 is $CO(CH_2)_{14}CH_3$ is even more preferred, the compound hexadecanoic acid-[1-hydroxymethyl-2-(1-hydroxy-2-oxo-cyclohex-3-enyl)ethyl]amide (13) being most preferred.

The term "pharmaceutically compatible salt" comprises the salts of inorganic acids, such as hydrochloride, hydrobromide, sulfate, perchlorate, nitrate and phosphate, as well as the salts of organic acids, e.g. acetate, oxalate, tartrate, citrate, succinate, maleate and fumarate.

The compounds according to the invention can be produced using the method described in below Examples 1 to 3. Their therapeutic suitability, i.e. the inhibition of the membrane-bound neutral sphingomylinase (SMase) or the influence of the intracellular ceramide concentration can be determined by known methods; see e.g.[1,2,8,9].

The present invention also relates to pharmaceutical preparations which contain a pharmacologically active amount of a compound according to the invention together with a pharmaceutically compatible carrier. Suitable carriers and the formulation of such pharmaceutical preparations are known to the person skilled in the art. Suitable carriers comprise e.g. phosphate-buffered common salt solutions, water, emulsions, e.g. oil/water emulsions, wetting agents, sterile solutions, etc. The pharmaceutical preparation according to the invention can be available in the form of an injection solution, tablet, ointment, suspension, emulsions a suppository, etc. It can also be administered in the form of depots (microcapsules, zinc salts, liposomes, etc.). The kind of administration of the pharmaceutical preparation depends inter alia on the form in which the active substance is available, it may be oral or parenteral. The methods of parenteral administration comprise the topical, intra-arterial, intramuscular, intramedullary, intrathekal, intraventricular, intravenous, intraperitoneal, transdermal or transmucosal (nasal, vaginal, rectal, sublingual) administration. The administration can also be made by microinjection. The suitable dose is determined by the attending physician and depends on various factors, e.g. on the patient's age, sex and weight, the kind and stage of the disease, e.g. AIDS, the kind of administration, etc.

Finally, the present invention also relates to the use of a compound according to the invention for treating a disease which is correlated with an increased ceramide concentration or in which a reduction of the ceramide concentration is desirable. This is preferably sepsis, a disease of the rheumatic form, atherosclerosis, a neurodegenerative disease such as Alzheimer's or Parkinson's disease, ischemia, apoplexy, myocardial infarction or AIDS. The antiapoptotic activity of the compounds according to the invention is shown in FIG. 3.

(b) Synthesis of the silyl enol ethers 8 and/or 9 a) HMDS, TMSI, 0–25° C., THF, 2 h, 89%.

(c) Asymmetric hydroxylation. A) AD-mix-β, $NaHOC_3$, $OsO_4$, tert.-$BuOH:H_2O$=1:1, 0° C.–25° C., 36 h, 58%.

(d) Synthesis of scyphostatin analogues A) TFA, $CH_2Cl_2$, $H_2O$, RT, 4 h, 89%; b) $CH_3(CH_2)_{14}COCl$, $Et_3N$, THF, –78° C., 91%.

Figure 3:
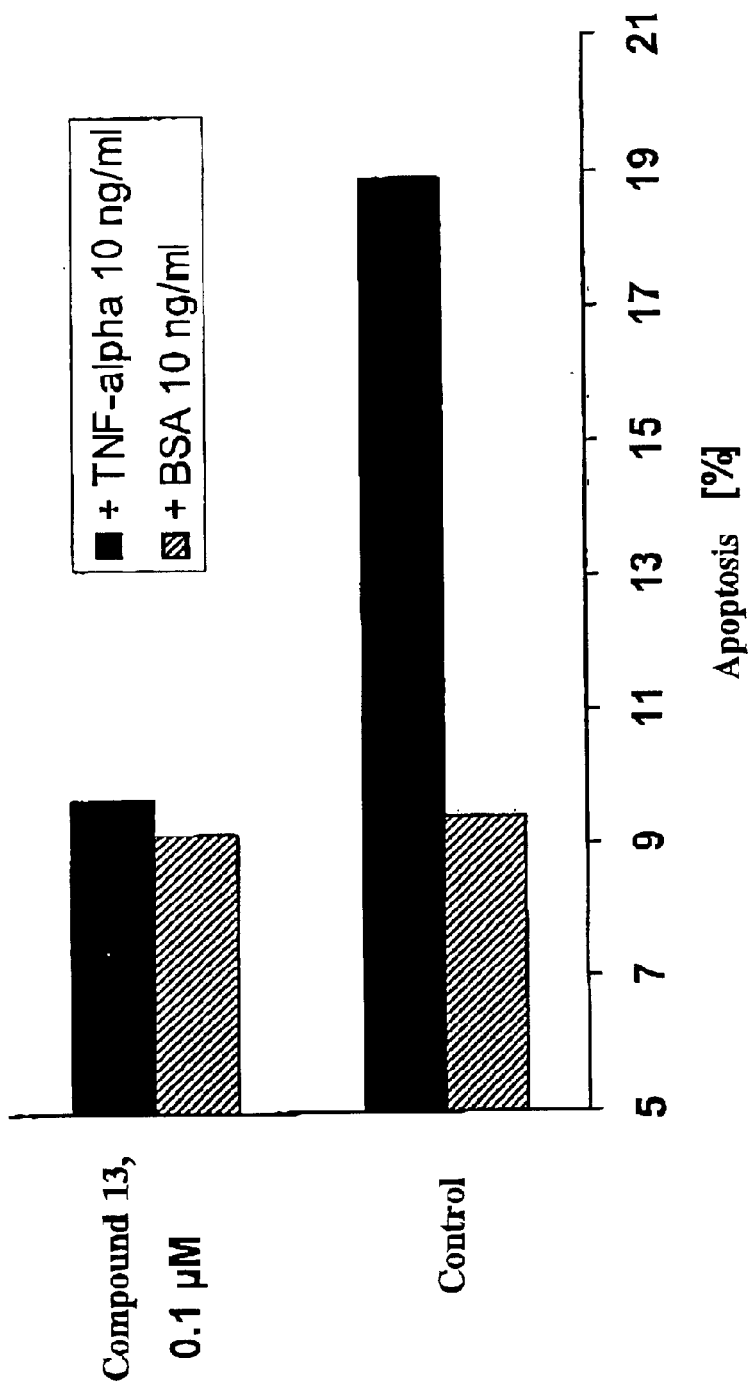

FIG. 3: Antiapoptotic activity of compound 13 in human monocytes Human monocytes are treated with tumor necrosis factor α (TNFα) or with albumin (controls) for 4 hours. In addition, part of the cells are pretreated with compound 13 (30 min., 0.1 μm). The percentage of apoptotic cells is determined in all of the samples by YOPRO-1 staining[10]. Average values from 5 experiments.

Figure 4:
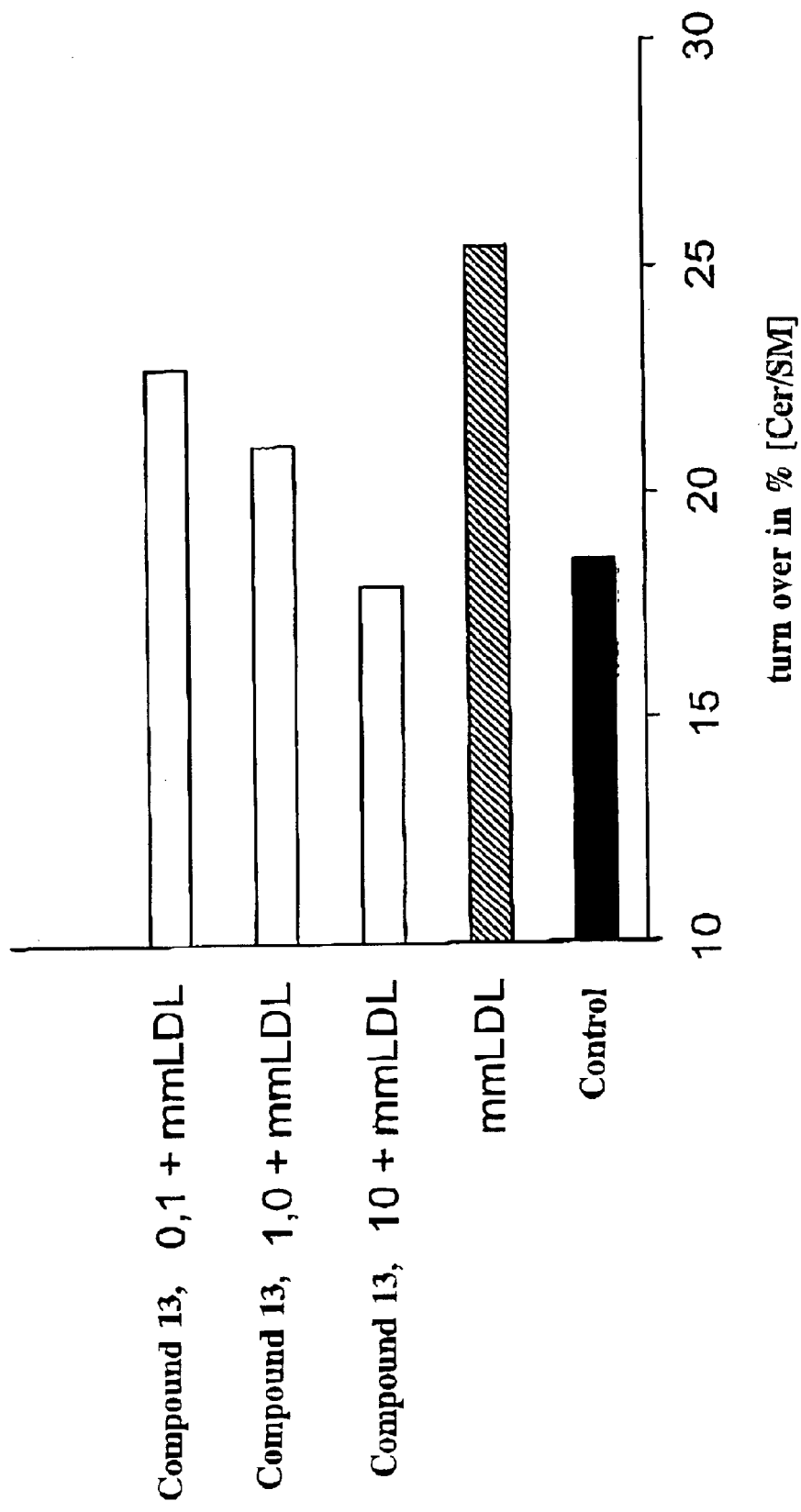

FIG. 4: Inhibitory effect of compound 13 (0.1–0 μm) on the sphingomyleinase activity of mmLDL-stimulated monocytes. Average values from 5 individual experiments.

The below examples explain the invention.

EXAMPLE 1

Synthesis of a Cyclohexenone Unit

Simlplified structural analogues of the cyclohexenone unit of scyphostatin were produced. The synthesis of the cyclohexenone unit wherein R1=R2=R3=R5=R6=H and R4=CO(CH$_2$)$_{14}$CH$_3$ is described by way of example.

Figure 1:
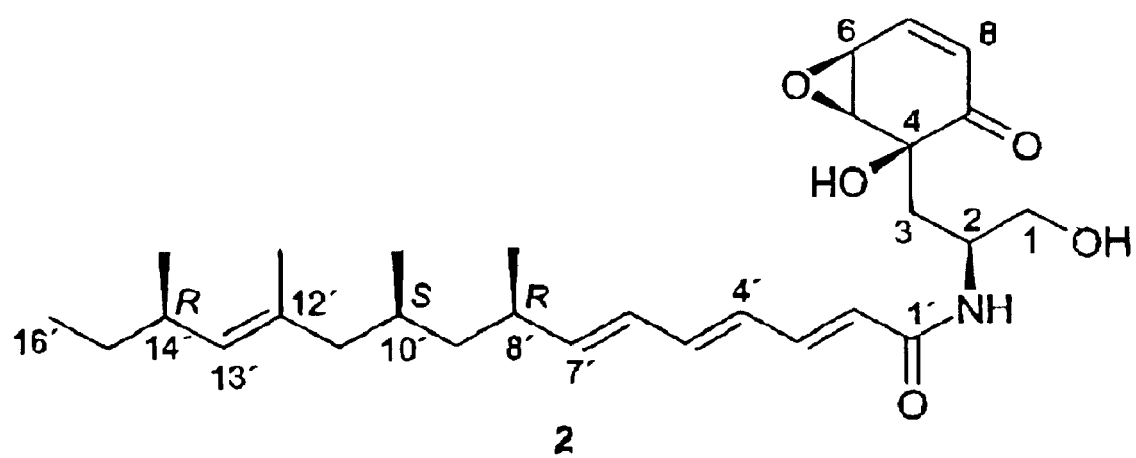
FIG. 1: Naturally occurring scyphostatin (2)
Figure 2:
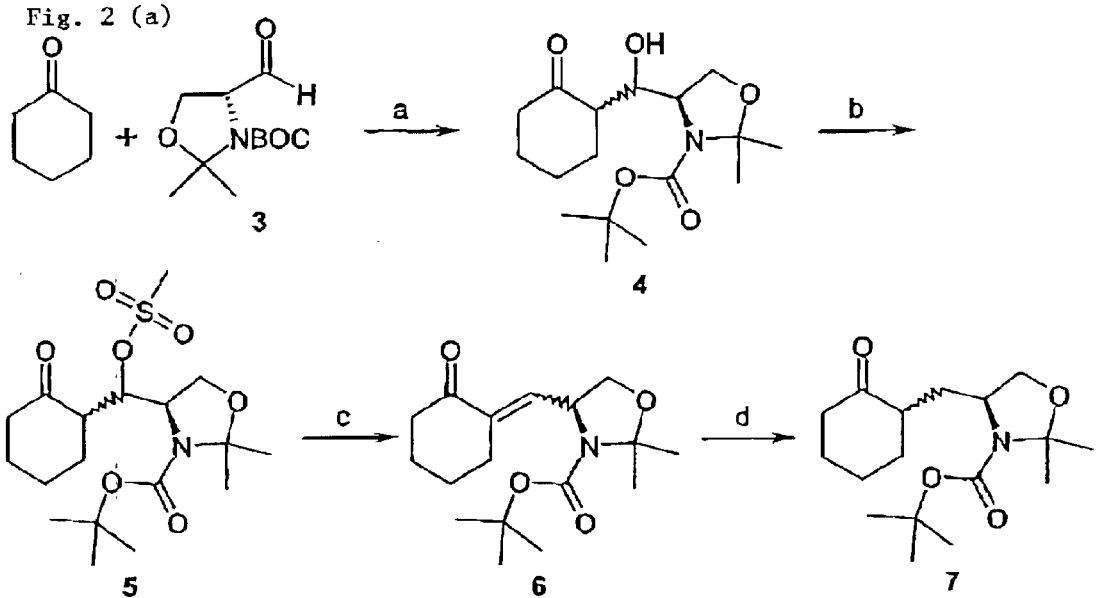
FIG. 2: synthesis of a cyclohexenone unit (a) Production of compound (7): a) LDA, THF, –78° C./2 h, RT/1 h, 84%; b) $Et_3N$, MsCl, $CH_2Cl_2$, 0° C., 2 h, 98%; c) DBU, $CH_2Cl_2$, 0° C./1 h, RT/12 h, 73%; d) Pd/C, $H_2$, 1 atm, EtOH, (96%), 30 ml 90%.
Figure 2:
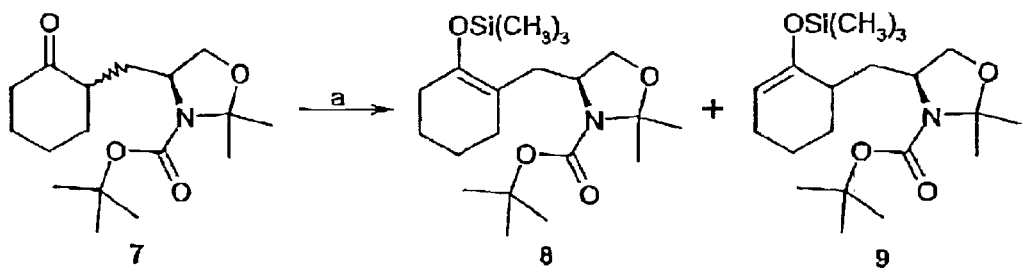
Figure 2:
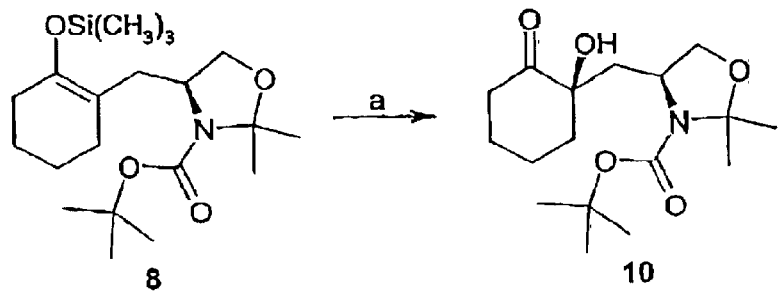
Figure 2:
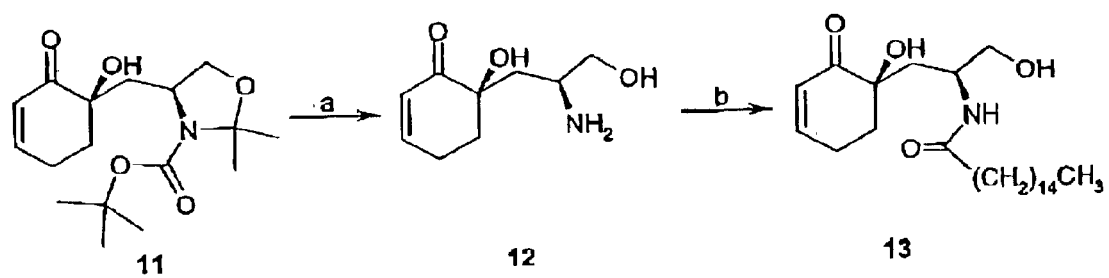

The below description of the method refers to FIG. 2.

Cyclohexanone and/or its lithium enolate and aldehyde 3 were converted into alcohol 4 in high yields (FIG. 2a). The α,β-unsaturated ketone 6 was obtained by mesitylation of this alcohol and subsequent elimination[3] using DBU. This ketone was hydrogenated to give ketone 7 using palladium on activated carbon in 96% ethanol.

When aldehyde 3 was coupled to cyclohexanone, the required (S)-stereochemistry was obtained on the amino-substituted C atom due to a change in the priorities. (Based on aldehyde 3b derived from L-serine, the (R) configured compound 4b was obtained.)

As a result of converting the substituted cyclohexanone 7 into the silylenol ether 8 (FIG. 2b) and subsequent asynmetric hydroxylation thereof it was also possible to obtain this substituted cyclohexanone C atom in (S)-stereochemistry. The corresponding (R)-isomers were accessible analogously, so that all of the isomers (RS, RR, SR, SS) could be generated. Using hexamethyldisilazane and trimethlsilyliodide it was possible to obtain the thermodynamically more stable enol ether 8 as compared to the kinetic product 9 at a ratio of 85, 15[4], which was determined by means of the $^1$H-NMR data. Both enol ethers 8 and 9 were separated by means of chromatography.

The asymmetric hydroxylation of the silyl enol ether 8 to give α-hydroxy ketone 10 was possible by means of the method described by Sharpless[5] using an AD-mix-β enriched with osmium(VIII)oxide in a basic environment (FIG. 2c). It was possible to detect the proper (S)-stereochemistry by comparison with the NMR data[1] determined by the natural substance. A NOE experiment conducted also supported the presence of (S)-stereochemistry. When AD-nix (J. Org. Chem. 1992, 57, page 2768; Aldrichimica Acta 1994, 27, 70) or the individual components contained therein were used, the (R)-enantiomer was obtained at the same order.

The corresponding α-bromine derivative was obtained from 10 by bromination[6] and converted into cyelohexenone 11 by dehydrobrominatiori using DBU[7].

The, amino alcohol 12 was obtained by deprotecting the cyclohexenone unit 11. This amino alcohol 12 was converted at −78° C. by reaction with electrophiles such as acid chlorides into scyphostatin analogues such as compound 13 (FIG. 2d).

It turned out that epoxide-free scyphostatin analogues such as 13 distinguish themselves by an increased chemical stability (e.g. stability in acidic solutions) and that analogues having substituents (NHR, R═CO(CH$_2$)$_n$ such as 13 and R═(CH$_2$)$_n$—R2 (R2=aryl, heteroaryl etc.) also distinguish themselves by redox stability (e.g. oxidation by oxygen). The inventors found that compounds such as 13 are stable with pH values of 2 at 40° C. for a period of several hours.

EXAMPLE 2

Production of 2,2-dimethyl-4-(2-oxocyclohexylmethyl)oxazolidine-3-Aarboxylic acid-tert.-butylester (7)

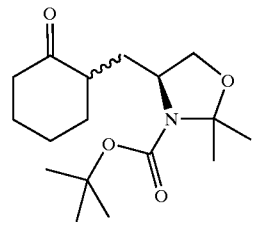

A suspension of 1.39 g 2,2-dimethyl-4-(2-oxo-cyclohexylidene methyl)oxazolidine-3-carbocxylic acid-tert.-butyl ester (6) (4.52 mmol) and 100 mg palladium on carbon in 50 ml ethanol (96%) were hydrogenated for 30 minutes. Thereafter, the catalyst was filtered off on Celite and the solution was concentrated. Following purification by means of column chromatography (silica gel//ether: n-hexane=3:1) the product was obtained as a colorless viscous oil yield: 1.41 g=90%; R$_f$ value −0.72), $^1$H-NMR (CDCl$_3$): δ in ppm=1.43 (s, 6H; C(CH$_3$)$_2$), 1.51 (s, 9H; C(CH$_3$)$_3$), 1.60–2.38 (m, 11H; C$_7$H$_{11}$O), 3.78 (d, 2H, $^3$J=7.51 Hz; CHCH$_2$O), 3.98 (m, 1H; CH$_2$CHN). $^{13}$C-NMR (CDCl$_3$): δ in ppm=24.65 (CH$_2$), 26.36 (CH$_2$), 27.26 (C(CH$_3$)$_2$), 28.37 (C(CH$_3$)$_3$), 31.14 (CHCH$_2$CH), 33.69 (CH$_2$), 46.11 (CH$_2$CHCO), 55.84 (CHN), 67.89 (OCH$_2$CH), 79.82 (C(CH$_3$)$_3$), 93.58 (C(CH$_3$)$_2$), 152.54 (COOC(CH$_3$)$_3$), 212.13 (CO). MS (EI, 60° C.), m/z (%)=311 (0.61) [M$^+$], 253 (1.91) [M$^+$-C$_4$H$_9$$^+$], 196 (34.95) [C$_{10}$H$_{14}$NO$_3$$^+$], 180 (7.77) [C$_5$H$_{14}$NO$_2$$^+$], 57 (100.0) [C$_4$H$_9$$^+$], IR (film): v̄=2930(s), 2858 (s), 1711 (s), 1699 (s), 1449 (s), 1388 (s), 1175 (s), 1094 (m), 921 (m) cm$^{-1}$.

| Elemental analysis: C$_{17}$H$_{29}$NO$_4$ (311.42 g/mol) [%] | | |
|---|---|---|
| Calc. | C 65.57 | H 9.38 | N 4.50 |
| Found | C 65.68 | H 9.27 | N 4.77 |

EXAMPLE 3

Production of Hexadecanoic Acid-[1-hydroxymethyl-2-(-hydroxy-2-oxo-cyclohex-3-enyl)ethyl]amide (13)

145 mg 12 (0.79 mmol) were dissolved in 50 ml THF, 1 ml triethylamine was added and the solution was cooled to −78° C. Then, 217 mg palmitic acid chloride (0.79 mmol, 0.24 ml) in 5 ml THF were slowly added dropwise and the solution was stirred at −78° C. for 15 minutes. The reaction was concluded using 25 ml saturated sodium hydrogencarbonate solution and the solution was extracted three times with 30 ml acetic ester each. The combined organic phases were washed with 30 ml water. Following drying on magnesium sulfate, concentration up to dryness was carried out in vacuo. Crude 13 in the form of a slightly yellowish solid was obtained. It was pulverized with cold ether and sucked off so as to obtain pure 13 as a colorless solid (yield: 302 mg=91%).

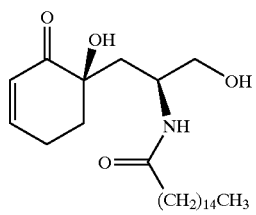

$^1$H-NMR (CDCl$_3$): δ in ppm=0.90 (t, 3H, $^3$J=6.63 Hz; CH$_3$); 1.24–2.21 (m, 34H; 17CH$_2$), 3.27 (b, 2H; 2OH), 3.48 (d, 1H, $^3$J=9.69 Hz; CH$_2$OH), 4.18 (m, 1H, CHNH$_2$), 5.88 (b, 1H; NHCO), 6.10 (d, 1H, $^3$J=9.68 Hz; CHCHCO), 7.01 (m, 1H; CHCHCO). $^{13}$C-NMR (CDCl$_3$): δ in ppm 13.89 (CH$_3$), 22.32–40.15 (17CH$_2$), 49.41 (CHN), 65.21 (HOCH$_2$CH), 78.85 (COH), 128.95 (COCH), 147.33 (CHCHCO), 200.88 (CO). MS (EI, 58° C.), m/z (%)=424 (0.82 [M$^+$], 407 (2.31 [M$^+$-OH], 239 (27.88) [C$_{16}$H$_{31}$O$^+$], 185 (7.46) [M$^+$-C$_{16}$H$_{31}$O], 94 (8.95) [C$_6$H$_6$O$^+$]. IR (film): ṽ=3436 (s), 3051 (m), 2977 (s), 2919 (s), 1710 (s), 1635 (s), 1467 (m), 1219 (s), 1122 (s), 1087 (s), 870 (m) cm$^{-1}$.

| Elemental analysis: C$_{25}$H$_{45}$NO$_4$ (423.63 g/mol) [%] | | | |
|---|---|---|---|
| Calc. | C 70.88 | H 10.71 | N 3.31 |
| Found | C 70.63 | H 10.58 | N 3.53 |

EXAMPLE 4

Sphingomyclinase Activity in Human Monocytes 90 nM BODIPY-FL-C$_5$ sphingomylein (molecular probes) are dissolved in 200 µl ethanol, then injected into 10 ml PBS containing 0.75 mg/ml BSA. The solution is dialyzed extensively against PBS, the resulting dialyzate is sterile-filtered and diluted 1:1 using RPMI medium. Together with the solution a monolayer of human monocytes' is incubated with 5% CO$_2$ at 37° C. for 4 hours, washed twice with 5 ml PBS, admixed with new medium and then incubated at the corresponding concentrations of compound (13) for 30 minutes. The pretreated cells are treated with slightly modified low-density lipoprotein (mmLDL)[10] for 4 hours and extracted according to Bligh and Dyer[11]. The enzyme activity is determined by the ratio of BODIPY-FL-C$_5$—sphingomyelin to BODIPY-FL-C$_5$ ceramide[12].

The results of the experiment are shown in FIG. 4.

LIST OF REFERENCES

[1] a) M. Tanaka, F. Nara, K. Suzuki-Konagai, T. Hosoya, T. Ogita, *J. Am. Chem. Soc.*, 1997, 119, 7871; b) F. Nara, M. Tanaka, T. Hosoya, K. Suzuki-Konagai, T. Ogita, *J. Antibiot.*, 1999, 52, 525.
[2] S. Saito, N. Tanaka, K. Fujimoto, H. Kogen, *Org. Lett.*, 2000, 2, 505.
[3] a) M. Suzuki, Y. Oda, N. Hamanaka, R. Noyori, *Heterocycles*, 1990, 30, 517; b) D. Meng, S. J. Danishefsky, *Angew. Chem.*, 1999, 111, 1582; c) H. Nagata, K. Ogasawara, *Tetrahedron Lett.*, 1999, 40, 6617.
[4] R. D. Miller, D. R. McKeala, *Synthesis*, 1979, 730.
[5] a) K. Morikawa, J. Payk, P. G. Andersson, T. Hashiyama, K. B. Sharpless, *J. Am. Chem. Soc.*, 1993, 115, 8463; b) H. C. Kolb, M. S. VanNieuwenzhe, K. B. Sharpless, *Chem. Rev,* 1994, 94, 2483.
[6] D. H. R. Barton, J. Boivin, M. Gastiger, J. Morzycki, R. S. Hay-Motherwell, W. B Motherwell, N. Ozbalik, K. H. Schwartzentruber, *J. Chem. Soc. Perkin, Trans.* 1, 1986, 947.
[7] J. P. Dulcère, J. Crandall, R. Faure, M. Santelli, V. Agati, M. N. Mihoubi, *J. Org. Chem.,* 1993, 58, 5702
[8] M. Harada-Shiba, M. Kinoshita, H. Kamido, K. Shimokado, *J. Biol. Chem.,* 1998, 273, 9681.
[9] S. Kirschnek, F. Paris, M. Weller, H. Grassme, K. Ferlinz, A. Riehle, Z. Fuks, R. Kolesnick, E. Gulbins *J. Biol. Chem.,* 2000, 275, 27316.
[10] R. Kinscherf, R. Claus, M. Wagner, The FASEB J. 1998, 12, 461–467
[11] E. G. Bligh und W. J. Dyer, Can. J. Biochem. Physiolol. 1959, 3, 911–917
[12] R. Kinscherf, R. Claus, H. P. Deigner, FEBS Lett. 1997, 405, 55–59

What is claimed is:

1. A compound formula

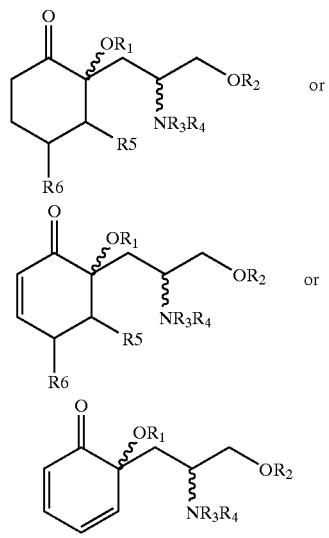

wherein:

each of R1, R2, R3, R5 and R6, which may be the same as or different from one another, is independently selected from among hydrogen, OH, SH, O-alkyl, O-aryl, O-acyl, sulfonic acid residues, thioalkyl, thiophenyl, alkyl, alkenyl, alkinyl, aryl, acyl and halo; and R4 is selected from among fatty acid residues, C$_6$–C$_{20}$ alkyl, alkenyl, alkinyl and aryl; or a pharmaceutically compatible salt thereof.

2. The compound according to claim 1, wherein the sulfonic acid residue is OSO$_2$CH$_3$.

3. A compound formula:

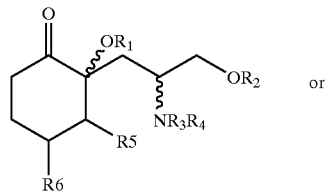

-continued

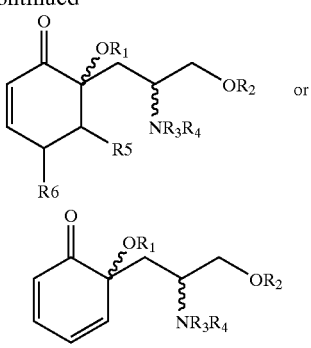

wherein:
each of R1, R2, R3, R5 and R6 is hydrogen, and R4 is selected from among fatty acid residues, $C_6$–$C_{20}$ alkyl, alkenyl, alkinyl and aryl; or a pharmaceutically compatible salt thereof.

4. A compound formula

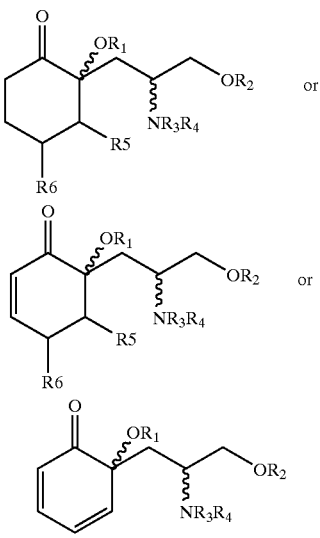

wherein
R1, R2, R3, R5 and R6, which may be the same as or different from one another, is independently selected from among hydrogen, OH, SH, O-alkyl, O-aryl, O-acyl, sulfonic acid residues, thioalkyl, thiophenyl, alkyl, alkenyl, alkinyl, aryl, acyl and halo; and R4 is $CO(CH_2)_{14}CH_3$.

5. The compound according to claim 4, which is hexadecanoic acid-(1-hydroxymethyl-2-(1-hydroxy-2-oxo-cyclohex-3-enyl)ethyl]amide.

6. A pharmaceutical preparation, comprising a pharmacologically active amount to reduce ceramide concentration of a compound according to claim 1 together with a pharmaceutically compatible carrier.

7. A method of reducing ceramide concentration, the method comprising administering to a subject an effective amount of a compound according to claim 1 for treating a condition selected from the group consisting of disease states associated with an increas d ceramide concentration.

8. The method according to claim 7, wherein the disease state is selected from the group consisting of sepsis, rheumatic disease, atherosclerosis, neurodegenerative disease, ischemia, apoplexy, myocardial infarction and AIDS.

9. A compound formula:

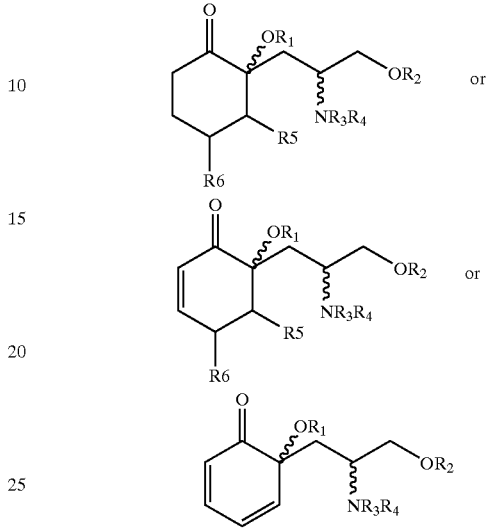

wherein: each of R1, R2, R3, R5 and R6 is hydrogen, and R4 is $CO(CH_2)_{14}CH_3$.

10. A pharmaceutical preparation, comprising a pharmacologically active amount to reduce ceramide concentration of a compound according to claim 4 together with a pharmaceutically compatible carrier.

11. A method of reducing ceramide conc ntration, the method comprising administering to a subject an effective amount of a compound according to claim 10 for treating a condition selected from the group consisting of disease states associated with an increased ceramide concentration.

12. The method according to claim 11, wherein the disease state is selected from the group consisting of sepsis, rheumatic disease, atherosclerosis, neurodegenerative disease, ischemia, apoplexy, myocardial infarction and AIDS.

13. A pharmaceutical preparation, comprising a pharmacologically active amount to reduce ceramide concentration of a compound according to claim 3 together with a pharmaceutically compatible carrier.

14. A method of reducing ceramide concentration, the method comprising administering to a subject an effective amount of a compound according to claim 3 for treating a condition selected from the group consisting of disease states associated with an increased ceramide concentration.

15. The method according to claim 14, wherein the disease state is selected from the group consisting of sepsis, rheumatic disease, atherosclerosis, neurodegenerative disease, ischemia, apoplexy, myocardial infarction and AIDS.

* * * * *

UNITED STATES PATENT AND TRADEMARK OFFICE
CERTIFICATE OF CORRECTION

PATENT NO. : 6,790,992 B2
DATED : September 14, 2004
INVENTOR(S) : Deigner, Hans-Peter It is certified that error appears in the above-identified patent and that said Letters Patent is hereby corrected as shown below:

Column 1,
Line 15, "sphingoxnyetin" should be -- "sphingomyelin" --
Line 41, "types" should be -- types. --
Line 66, "apoptosis'" should be -- apoptosis --

Column 2,
Line 61, "SMC," should be -- SMC. --

Column 3,
Line 4, "generation)" should be -- generation --

Column 4,
Line 14, "halogen;" should be -- halogen --
Line 60, "berizvalene" should be -- benzvalene --

Column 5,
Line 1, "tetazolyl" should be -- tetrazolyl --
Line 18, "propytoxy" should be -- propyloxy --

Column 6,
Line 47, "30 mi" should be -- 30 min. --

Column 7,
Line 35, "85, 15$^4$" should be -- 85:15 --
Line 53, "dehydrobrominatiori" should be -- dehydrobromination --

Column 8,
Line 26, "-0.72)," should be -- =0.72). --
Line 36, "M"-$C_4H_9$-$^+$" should be -- [$M^+$-$C_4H_9$] --

UNITED STATES PATENT AND TRADEMARK OFFICE
CERTIFICATE OF CORRECTION

PATENT NO.    : 6,790,992 B2
DATED         : September 14, 2004
INVENTOR(S)   : Deigner, Hans-Peter It is certified that error appears in the above-identified patent and that said Letters Patent is hereby corrected as shown below:

<u>Column 9,</u>
Line 33, "Sphingomyclinase" should be -- Sphingomyelinase --
Line 40, "monocytes'" should be -- monocytes --

<u>Column 12,</u>
Line 35, "conc ntration" should be -- concentration --

Signed and Sealed this

First Day of March, 2005

JON W. DUDAS
*Director of the United States Patent and Trademark Office*